United States Patent [19]

O'Leary et al.

[11] Patent Number: 5,484,601
[45] Date of Patent: Jan. 16, 1996

[54] FLOWABLE DEMINERALIZED BONE POWDER COMPOSITION AND ITS USE IN BONE REPAIR

[75] Inventors: Robert K. O'Leary, Spring Lake, N.J.; Patrick A. McBrayer, Yardley, Pa.

[73] Assignee: Osteotech, Inc., Shrewsbury, N.J.

[21] Appl. No.: 779,401

[22] Filed: Oct. 18, 1991

Related U.S. Application Data

[63] Continuation of Ser. No. 410,596, Sep. 21, 1989, Pat. No. 5,073,373.

[51] Int. Cl.⁶ ..................... A61K 35/32
[52] U.S. Cl. ............ 424/422; 424/94.1; 424/184.1; 424/423; 424/520; 424/549; 424/562; 514/772.2; 514/772.3; 514/772.6; 514/774; 514/777; 514/781; 514/778; 514/785; 514/801; 514/802
[58] Field of Search ................ 424/422, 423, 424/549, 602; 623/16

[56] References Cited

U.S. PATENT DOCUMENTS

| | | | |
|---|---|---|---|
| 4,191,747 | 3/1980 | Scheicher | 424/549 |
| 4,430,760 | 2/1984 | Smestad | 3/1.9 |
| 4,440,750 | 3/1984 | Glowacki et al. | 424/549 |
| 4,563,489 | 1/1986 | Urist | 524/21 |
| 5,053,049 | 10/1991 | Campbell | 623/16 |
| 5,073,373 | 12/1991 | O'Leary et al. | 424/422 |

FOREIGN PATENT DOCUMENTS

| | | | |
|---|---|---|---|
| 0082621 | 6/1983 | European Pat. Off. | |
| 0880425 | 11/1981 | U.S.S.R. | 424/549 |

Primary Examiner—Thurman K. Page
Assistant Examiner—James M. Spear
Attorney, Agent, or Firm—Dilworth & Barrese

[57] ABSTRACT

A flowable demineralized bone powder composition is provided for use in surgical bone repair.

13 Claims, No Drawings

FLOWABLE DEMINERALIZED BONE POWDER COMPOSITION AND ITS USE IN BONE REPAIR

This is a continuation of application Ser. No. 07/410,596 filed Sep. 21, 1989, now U.S. Pat. No. 5,073,373

BACKGROUND OF THE INVENTION

This invention relates to a flowable demineralized bone powder composition and to the use of the composition in the surgical repair of bone defects.

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein" *Orthopaedic Review*, Vol. XVII, No. 8, pp. 857–863 (August, 1989).

According to Habal et al., "Autologous Corticocancellous Bone Paste for Long Bone Discontinuity Defects: An Experimental Approach", *Annals of Plastic Surgery*, Vol. 15, No. 2, pp. 138–142 (Aug. 1985), autogenous bone which has been granulated into a pastelike material and combined with autogenous blood has been used in the repair of long bone defects in dogs.

SUMMARY OF THE INVENTION

It is an object of the invention to provide a flowable demineralized bone powder composition for use in surgical bone repair.

It is a particular object of the invention to provide a composition of liquid or pastelike consistency comprising demineralized osteogenic bone powder and a biocompatible liquid synthetic organic material as a carrier for the bone powder with or without such optional ingredients as thixotropic agents, medicaments, and the like, and to apply the composition at a bone defect site to induce new bone ingrowth at the site.

It is another particular object of the invention to provide as the carrier component of such a composition a biocompatible liquid polyhydroxy compound or ester thereof, e.g., glycerol or glycerol monoacetate (monoacetin).

In keeping with these and related objects of the invention, there is provided a flowable composition comprising demineralized osteogenic bone powder and a biocompatible liquid synthetic organic material as carrier therefor.

Application of the foregoing composition to the site of a bone defect, e.g., one resulting from injury, infection, malignancy or developmental malformation, leads to rapid new bone ingrowth by one or more mechanisms such as osteogenesis, osteoconduction and osteoinduction.

The bone powder composition of this invention can be readily prepared when and as needed, preferably with the components of the composition, the means for their combination to provide the composition and the means for applying the composition to a bone defect site being provided in the form of a unitary kit. Alternatively, the bone powder composition can be prepared beforehand and stored in the sterile condition for later use, optionally within the means which will be used to apply the composition to the bone defect site.

DESCRIPTION OF THE PREFERRED EMBODIMENTS

The demineralized pulverized or powdered bone component of the composition herein is a known type of material and is prepared in accordance with known procedures The expressions "pulverized bone", "powdered bone" and "bone powder" as used herein shall be understood to include bone particles of a wide range of average particle size ranging from relatively fine powders to coarse grains and even larger chips. So, for example, the bone powder present in the composition of this invention can range in average particle size from about 0.1 to about 1.2cm and preferably from 0.2 to 1cm. The bone powder can be obtained from cortical, cancellous and/or corticocancellous allogeneic or xenogeneic bone tissue. In general, allogeneic bone tissue is preferred as the source of the bone powder.

In a preferred bone demineralization procedure, the bone is first pulverized to the desired average particle size followed by defatting/disinfecting and acid demineralization treatments. A preferred defatting/ disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably 70% alcohol. Following defatting, the bone is immersed in acid over time to effect demineralization. Acids which can be employed in this operation include inorganic acids such as hydrochloric acid and organic acids such as peracetic acid. After acid treatment, the bone powder is rinsed with water for injection, buffered with a buffering agent to a final predetermined pH and then finally rinsed with water for injection to remove residual amounts of acid and buffering agent. The demineralized bone powder can be used immediately for preparation of the composition of this invention or it can be stored under aseptic conditions, advantageously in a freeze-dried state, prior to such preparation.

If desired, the bone powder can be modified in one or more ways, e.g., the porosity of the bone powder can be increased and/or the bone powder can be treated with one or more modifying agents, e.g., glutaraldehyde, as disclosed in U.S. Pat. No. 4,678,470. Another optional treatment involves the augmentation of the bone protein content of the powdered bone employing the procedure of U.S. Pat. No. 4,743,259.

Any of a variety of substances can be introduced into the bone particles, e.g., by soaking or immersing the bone particles in a solution of the desired substance(s) followed by drying of the bone particles. Substances which can be readily incorporated in the bone particles in this or any other suitable manner include antiviral drugs, e.g., those suitable for preventing transmission of acquired immune deficiency syndrome (AIDS); antimicrobials and/or antibiotics such as erythromycin, bacitracin, neomycin, penicillin, polymyxin B, tetracyclines, viomycin, chloromycetin and streptomycins, cefazolin, ampicillin, tobramycin, clindamycin and gentamycin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer-cell scaffolds with parenchymal cells; angiogenic drugs and polymeric carriers containing such drugs; collagen lattices; biocompatible surface active agents; antigenic agents; cytoskeletal agents; biologically active components such as bone morphogenetic proteins (BMPs), transforming growth factor (TCF-beta), insulin-like growth factor (IGD-1); mesenchymal elements; bone digesters; antitumor agents; cellular attractants and attachment agents; immunosuppressants; permeation enhancers, e.g., fatty acid esters such as the laurate, myristate and stearate monoesters of polyethylene glycol, enamine derivatives, alpha-keto aldehydes, etc.; and, nucleic acids. The amounts of optionally added substances can vary widely with optimum levels being readily determined in a specific case by routine experimentation.

To provide the demineralized allogeneic bone powder composition of this invention, the demineralized bone powder with or without any of the foregoing optional components mentioned above absorbed therein is combined with a biocompatible liquid synthetic organic material which functions as a carrier or suspension agent for the bone powder.

The term "liquid" as employed herein is intended to include (1) organic materials which in the pure or highly concentrated state and at ambient temperature, e.g., 15°–40° C. are flowable liquids and (2) organic materials which in the pure or concentrated state and at ambient temperature are normally solid but dissolved in a suitable solvent, e.g., water or a biocompatible organic solvent such as ethanol, can be provided in liquid form. Functionally, the liquid component of the composition serves to provide a flowable material of widely varying consistency. The term "flowable" as used herein applies to compositions whose consistencies range from those which can be described as shape-sustaining but readily deformable, e.g., those which behave like putty, to those which are runny. Specific forms of flowable bone powder compositions include cakes, pastes, creams and fillers. Suitable carriers for the bone powder include liquid polyhydroxy compounds and their esters, polysaccharides, surface active agents, and the like, the polyhydroxy compounds being preferred. The preferred class of polyhydroxy compounds possesses up to about 12 carbon atoms and where their esters are concerned, are preferably the monoesters and diesters. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. Of these, glycerol is especially preferred as it exhibits a particularly pronounced capability for dissolving osteogenic proteins present in the bone powder and enhancing the availability of these proteins at the bone repair site. Mixtures of the afore-discussed polyhydroxy compounds or esters, e.g., sorbitol dissolved in glycerol, glycerol combined with monoacetin and/or diacetin, etc., are also useful.

Where, in a particular bone powder composition, the bone powder has a tendency to quickly or prematurely separate from the carrier or to otherwise settle out from the composition such that application of a fairly homogeneous composition is rendered difficult or inconvenient, it can be advantageous to include within the composition a substance whose thixotropic characteristics prevent or reduce this tendency. Thus, e.g., where the carrier component is glycerol and separation of bone powder occurs to an excessive extent where a particular application is concerned, a thickener such as a solution of polyvinyl alcohol, polyvinylpyrrolidone, cellulosic ester such as hydroxypropyl methylcellulose, carboxy methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, etc., can be combined with the carrier in an amount sufficient to significantly improve the suspension-keeping characteristics of the composition.

As previously indicated, the bone powder composition of this invention can be freshly prepared just prior to use by mixing of the bone powder, carrier and optional component(s) in any suitable sequence of separate mixing operations or all at once. Thus, the bone powder can be mixed with the optional ingredient(s) and thereafter combined with the liquid carrier component, the bone powder can be mixed with the carrier followed by addition of the optional ingredient(s) or the optional ingredients can be added to the carrier followed by addition of the bone powder. Variations of these sequences of mixing operations are, of course, possible. The amount of bone powder which can be incorporated into the composition of this invention can vary widely with amounts of from about 5 to about 80 weight percent, and preferably from about 20 to about 60 weight percent, being entirely suitable in most cases. To facilitate on-site preparation of the composition herein, the bone powder, preferably in lyophilized form, and carrier (the latter containing any of the optional ingredients identified above) can be stored in separate packages or containers under sterile conditions and brought together in intimate admixture at the moment of use for immediate application to a bone defect site employing any suitable means, e.g., a syringe, spatula, etc. U.S. Pat. No. 4,458,733, the contents of which are incorporate by reference herein, describes a combined storage, mixing and application device which can be adapted to perform the foregoing functions of storage, mixing and application. Alternatively, the bone powder composition can be prepared well in advance and stored under sterile conditions until required for use, e.g., in the barrel of a syringe or other suitable applicator device.

The bone powder composition of this invention can be applied to the bone defect in a variety of ways, e.g., by packing the site with the composition provided in the form of a highly viscous paste. Among the bone repair applications for which the use of the bone powder composition of this invention is eminently suited are: standard or custom arthroplasty prosthesis; reconstruction of skeletal or other osseous defects; enhancing or augmenting the effectiveness of internal and external fixation devices, bone plates, etc.; as a replacement of corticocancellous strips, and so forth.

The following example is illustrative of the preparation of the flowable demineralized allogeneic bone powder composition of this invention.

EXAMPLE

A quantity of allogeneic cortical or cancellous bone which has been pulverized and sieved to an average particle size of from about 100 to about 300 microns is introduced into a reactor which is then sealed. A 70% ethanol solution at the rate of 30 milliliters per gram of bone is introduced into the reactor followed by agitation for 1 hour (Bolander et al., *Journal of Bone and Joint Surgery*, Vol. 68-A, No. 8 (Oct. 1986)) to effect defatting and disinfecting of the bone powder. Following drainage of the ethanol, a 0.6N solution of HCl at a rate of 50 ml per gram of bone is introduced into the reactor (Bolander et al., ibid.), the reaction proceeding for 3 hours (Glowackie, *AATB Workshop*, 11th Annual meeting (1987)). Following drainage of the HCl, the bone is covered and rinsed three times with water for injection (WFI) with the WFI being replaced at 5 minute intervals. Following drainage of the WFI, the bone is completely covered with 0.1M sodium phosphate, a procedure which is repeated until the pH of the solution falls between 6.8 and 7.4. The rinsing procedure with WFI is repeated to provide demineralized cortical or cancellous bone powder ready for mixing with the carrier component to provide the flowable composition of this invention.

The foregoing demineralized bone powder, 25 gm, and injectable grade glycerol, 95 gm, were thoroughly mixed to provide a composition of pastelike consistency. The composition is readily applied to a bone defect site, e.g., employing a syringe or spatula.

What is claimed is:

1. A flowable composition for application to a bone defect site to promote new bone growth at the site which comprises a new bone growth-inducing amount of demineralized osteogenic bone powder in a biocompatible liquid polyhydroxy compound and/or ester thereof as a carrier for the bone powder.

wherein the liquid polyhydroxy compound and/or ester thereof is selected from the group consisting of glycerol monoesters and diesters of glycerol derived from low molecular weight carboxylic acids, ethylene glycol, diethylene glycol, triethylene glycol, 1,2-propanediol. trimethylolethane, trimethyolpropane, pentaerythritol, sorbitol, esters of any of the foregoing polyhydroxy compounds and mixtures thereof.

2. The composition of claim 1 containing at least one additional ingredient selected from bone morphogenetic proteins, transforming growth factor and insulin-like growth factor IGD-1.

3. A flowable composition for application to a bone defect site to promote new bone growth at the site which comprises a new bone growth-inducing amount of pulverized demineralized osteogenic bone powder in a biocompatible carrier for the bone powder, wherein said carrier is selected from the group consisting of glycerol, monoacetin, diacetin, and mixtures thereof, and wherein the composition contains at least one additional ingredient selected from bone morphogenetic proteins, transforming growth factor and insulin-like growth factor IGD-1.

4. The composition of claim 1 wherein the average particle size of the demineralized bone powder is from about 0.1 to about 1.2 cm.

5. The composition of claim 1 wherein the average particle size of the demineralized bone powder is from about 0.2 to about 1 cm.

6. The composition of claim 1 wherein the demineralized bone powder is derived from cortical, cancellous and/or corticocancellous allogeneic or xenogeneic bone tissue.

7. The composition of claim 1 containing from about 5 to about 80 weight percent demineralized bone powder.

8. The composition of claim 1 containing from about 20 to about 60 weight percent demineralized bone powder.

9. The composition of claim 1 containing at least one additional ingredient selected from the group consisting of antiviral agent, antimicrobial agent, antibiotic agent, amino acid, peptide, vitamin, protein synthesis co-factor, hormone, endocrine tissue, synthesizer, enzyme, polymer-cell scaffolding agent with parenchymal cells, angiogenic drug, polymeric drug carrier, collagen lattice, antigenic agent, cytoskeletal agent, mesenchymal agent, bone digester, antitumor agent, cellular attractant, cellular attachment agent, immunosuppressant, nucleic acid, surface active agent and penetration enhancer.

10. The composition of claim 1 wherein said polyhydroxy compound comprises sorbitol dissolved in a solvent selected from the group consisting of glycerol, monacetin and diacetin and mixtures thereof.

11. The composition of claim 1 additionally comprising a thickener selected from the group consisting of polyvinyl alcohol, polyvinylpyrrolidone, hydroxypropyl methylcellulose, carboxy methylcellulose, pectin, food-grade texturizing agent, gelatin, dextran, collagen, starch, hydrolyzed polyacrylonitrile, hydrolyzed polyacrylamide and polyacrylic acid salt and mixtures thereof.

12. The composition of claim 1 wherein said demineralized osteogenic bone powder has been subjected to acid demineralization treatment.

13. The composition of claim 12 wherein said demineralized osteogenic bone powder has additionally been subjected to defatting/disinfecting treatment.

* * * * *